United States Patent [19]

Wu

[11] Patent Number: 4,471,150

[45] Date of Patent: Sep. 11, 1984

[54] CATALYSTS FOR LIGHT OLEFIN PRODUCTION

[75] Inventor: Margaret M. Wu, Belle Mead, N.J.

[73] Assignee: Mobil Oil Corporation, New York, N.Y.

[21] Appl. No.: 521,639

[22] Filed: Aug. 10, 1983

Related U.S. Application Data

[63] Continuation of Ser. No. 335,982, Dec. 30, 1981, abandoned.

[51] Int. Cl.³ ............................................... C07C 1/00
[52] U.S. Cl. .................................................. 585/640
[58] Field of Search ......................................... 585/640

[56] References Cited

U.S. PATENT DOCUMENTS

| | | | |
|---|---|---|---|
| 3,911,041 | 10/1975 | Kaeding et al. | 260/682 |
| 3,979,472 | 9/1976 | Butter | 260/668 R |
| 4,049,573 | 9/1977 | Kaeding | 252/432 |
| 4,062,905 | 12/1977 | Chang et al. | 260/682 |
| 4,066,714 | 1/1978 | Rodewald | 260/682 |
| 4,079,095 | 3/1978 | Givens et al. | 260/682 |
| 4,079,096 | 3/1978 | Givens et al. | 260/682 |
| 4,086,186 | 4/1978 | Rubin et al. | 252/430 |
| 4,229,608 | 10/1980 | Chen et al. | 585/640 |
| 4,247,731 | 1/1981 | Wunder et al. | 585/640 |
| 4,278,565 | 7/1981 | Chen et al. | 585/640 |
| 4,296,266 | 10/1981 | Wunder et al. | 585/640 |

*Primary Examiner*—Curtis R. Davis
*Attorney, Agent, or Firm*—A. J. McKillop; M. G. Gilman; E. F. Kenehan, Jr.

[57] ABSTRACT

Modified zeolite catalyst compositions comprising a crystalline aluminosilicate zeolite having pore windows formed by 8-membered rings of oxygen atoms, e.g. ZSM-34, in combination with a magnesium oxide, manganese oxide or magnesium oxide/platinum oxide catalyst modifier. Such modified zeolite catalysts are especially useful for converting methanol and/or methyl ester to an olefin-containing hydrocarbon product enriched in ethylene and propylene with enhanced catalyst lifetime.

7 Claims, No Drawings

CATALYSTS FOR LIGHT OLEFIN PRODUCTION

This is a continuation of copending application Ser. No. 335,982, filed Dec. 30, 1981 now abandoned.

BACKGROUND OF THE INVENTION

1. Field of the Invention

This invention relates for improved zeolite catalysts suitable for converting methanol and/or methyl ether to light olefins.

2. Description of the Prior Art

A remarkable growth in the production of synthetic fibers, plastics and rubber has taken place in recent decades. Such growth, to a large extent, has been supported and encouraged by an expanding supply of inexpensive petroleum raw materials such as ethylene and propylene. However, increasing demand for these light olefins has, from time to time, led to periods of shortage, either due to a diminished supply of suitable feedstocks or to limited processing capacity. In any event, it is now considered highly desirable to provide efficient means for converting raw materials other than petroleum to light olefins.

One such non-petroleum source of light olefins is coal-derived methanol and methyl ether. In this respect, it is known that methanol or methyl ether can be catalytically converted to olefin-containing hydrocarbon mixtures by contact under certain conditions with particular types of crystalline zeolite catalyst materials. U.S. Pat. No. 4,025,575, issued May 24, 1977, to Chang et al and U.S. Pat. No. 4,083,889, issued Apr. 11, 1978 to Caesar et al, for example, both disclose processes whereby methanol and/or methyl ether can be converted to an olefin-containing product over a ZSM-5 type (constraint index 1–12) zeolite catalyst. ZSM-5, in fact, converts methanol and/or methyl ether to hydrocarbons containing a relatively high concentration of light ($C_2$ and $C_3$) olefins with prolonged catalyst lifetime before catalyst regeneration becomes necessary.

It is also known that other types of zeolite catalysts can be used to convert methanol and/or methyl ether to olefin-containing hydrocarbon products containing even higher proportions of light olefins than can be realized by methanol/methyl ether conversion over ZSM-5. For example, U.S. Pat. Nos. 4,079,095 and 4,079,096, both issued Mar. 14, 1978, to Givens, Plank and Rosinski, disclose that zeolites of the erionite-offretite type, and especially ZSM-34, can usefully be employed to promote conversion of methanol and/or methyl ether to products comprising a major amount of $C_2$ and $C_3$ light olefins. However, while erionite-offretite type catalysts are extremely selective to light olefins production, such smaller pore zeolites tend to age rapidly in comparison to ZSM-5 when used for methanol/methyl ether conversion. There is thus a continuing need to develop new catalyst compositions and systems suitable for selectively converting an organic charge comprising methanol and/or methyl ether to light olefin products with both high light olefin selectivity and enhanced catalyst lifetime.

Accordingly, it is an object of the present invention to provide novel zeolite catalysts which are useful for promoting conversion of methanol and/or methyl ether to olefin-containing products with high selectivity to production of light olefins.

It is a further object of the present invention to provide such selective catalysts having enhanced catalyst lifetime for methanol/methyl ether conversion.

It is a further object of the present invention to provide a methanol/methyl ether conversion process employing such catalysts and having high selectivity for production of light olefins and improved catalyst aging characteristics.

SUMMARY OF THE INVENTION

In accordance with the present invention, novel modified catalyst compositions are provided which are suitable for the selective conversion of methanol and/or methyl ether to light olefins with enhanced catalyst lifetime. Such modified catalysts essentially comprise at least some crystalline aluminosilicate zeolite material characterized by a crystalline structure having pore windows formed by 8-membered rings of oxygen atoms, e.g., offretite, erionite, chabazite, Zeolite T, Zeolite W and ZSM-34. Such catalysts further essentially comprise a minor proportion of a catalyst modifier which can be an oxide of magnesium, an oxide of manganese or a combination of an oxide of magnesium and an oxide of platinum. Methanol/methyl ether conversion processes employing such catalysts are also provided.

DETAILED DESCRIPTION OF THE INVENTION

The catalyst compositions of the present invention comprise particular types of crystalline aluminosilicate zeolite materials which can usefully be employed under particular reaction conditions to promote conversion of methanol and/or methyl ether to light olefins such as ethylene and propylene. Such zeolites have a crystal structure that provides constrained access to, and egress from, the intracrystalline free space by virtue of having a pore dimension which is usually greater than about $3.6 \times 3.7$ Angstroms. Such zeolites also generally have a Constraint Index substantially greater than 12. Zeolite material of this type has pore windows of about the size such as would be provided by 8-membered rings of oxygen atoms. It is to be understood that these rings are those formed by the regular disposition of the tetrahedra making up the anionic framework of the crystalline aluminosilicate zeolite, the oxygen atoms themselves being bonded to silicon (or aluminum) atoms at the centers of the tetrahedra.

It should also be understood that the zeolites useful herein include zeolite types which may contain some crystalline zeolitic material having pore windows of a size formed by oxygen atom rings containing more than 8 members. For example, a number of natural and synthetic zeolites are known to comprise intergrowths of more than one type of crystalline material. Thus a given zeolite may contain some crystalline material which has pore windows formed by 8-membered rings of oxygen atoms and some material having pore windows formed by 10- or 12-membered rings. The zeolites employed in the process of the instant invention are those which have at least a portion of their total crystalline zeolite material composed of zeolitic material having pore windows formed by 8-membered rings of oxygen atoms.

Zeolites which comprise at least some of the 8-membered ring crystalline zeolite material include those of the erionite-offretite family such as synthetic and natural erionite, synthetic and natural offretite, Zeolite T, Zeolite W, natural and synthetic chabazite and ZSM-34. Chabazite, erionite and offretite are all more particularly described in Meier and Olson, *Atlas of Zeolite Structure Types,* published in 1978 by the International Zeolite Association and the references cited therein. Zeolite T is described in U.S. Pat. No. 2,950,952 and Zeolite W is described in U.S. Pat. No. 3,012,853. All of these publications and patents are incorporated herein by reference.

A particularly preferred zeolite material for use in the catalyst compositions of the present invention is ZSM-34. ZSM-34 and its synthesis are more fully described in Rubin et al; U.S. Pat. No. 4,116,813, issued Sept. 26, 1978 and its parent U.S. Pat. No. 4,086,186, issued Apr. 25, 1978. These patents are also incorporated herein by reference.

ZSM-34 is a unique crystalline aluminosilicate zeolite, belonging to the erionite-offretite family, having the composition, as synthesized, and after drying of:

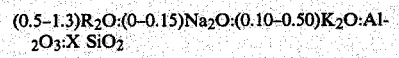

$$(0.5-1.3)R_2O:(0-0.15)Na_2O:(0.10-0.50)K_2O:Al_2O_3:X\ SiO_2$$

where R is the organic nitrogen-containing cation derived from choline $[(CH_3)_3NCH_2CH_2OH]$ and X is 8 to 50, preferably 8 to 30 and still more preferably 8 to 20. This zeolite, unlike other members of the erionite-offretite family, appears to have a tabular morphology and the capability, after calcination at 1000° F. for at least a period of time to remove the organic cation, of sorbing at least 9.5 weight percent of n-hexane, at ambient temperature and a n-hexane pressure of 20 mm. which is higher than that for any other known offretite or erionite. ZSM-34 is characterized by the X-ray powder diffraction pattern as set forth in the aforementioned U.S. Pat. No. 4,116,813 and U.S. Pat. No. 4,086,186.

All of the foregoing zeolites, as synthesized, may be calcined to remove the organic constituent ($R_2O$) and/or ion exchanged to replace the alkali metal ions with hydrogen ion precursor, e.g. ammonium, and/or other metal ions, particularly metals from Groups IB, IIA, IIB, IIIB, VIIA, VIII and the rare earth metals with only minor changes in the X-ray characterization and sorption properties. The ion exchanged products are catalytically active zeolites useful in the process of this invention.

In practicing the conversion process of the present invention, it may be desirable to incorporate the above-described crystalline aluminosilicate zeolites in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the small pore zeolites employed herein may be compounded with a porous matrix material, such as alumina, silica-alumina, silica-magnesia, silica-zirconia, silica-thoria, silica-beryllia, silica-titania, as well as ternary combinations, such as silica-alumina-thoria, silica-alumina-zirconia, silica-alumina-magnesia and silica-magnesia-zirconia. The matrix may be in the form of a cogel. The relative proportions of finely divided zeolite and inorganic oxide gel matrix may vary widely with the zeolite content ranging from between about 1 to about 99 percent by weight and more usually in the range of about 5 to about 80 percent by weight of the composite.

As discussed more fully hereinafter, catalyst compositions comprising zeolitic material of the 8-membered oxygen ring type as described above can be used to convert a charge comprising methanol (methyl alcohol) and/or methyl ether to hydrocarbons. Such catalysts are especially useful in directing this conversion reaction toward light ($C_2$ and $C_3$) olefin production and away from the formation of $C_4+$ hydrocarbons. In accordance with the present invention, it has been discovered that modification of such zeolites with particular types of metal oxides can enhance the lifetime of such zeolite catalysts when they are employed in this selective conversion of methanol and/or methyl ether to light olefins.

The zeolite catalysts herein are modified by incorporating thereon a minor proportion of an oxide of magnesium, an oxide of manganese or a combination of an oxide of magnesium and oxide of platinum. Such modified zeolite composites can be prepared by contacting the zeolite composition with one or more compounds or complexes of the elements to be incorporated and thereafter heating the composite to convert the modifying element to its oxide form. Incorporation can occur by the mechanisms of ion exchange, adsorption and/or impregnation, the latter two phenomena commonly being referred to as "stuffing." It should be emphasized that, while ion exchange can be used to incorporate the modifying metals onto the zeolite compositions described herein, ion exchange alone will generally not provide the requisite amount or form (i.e. the oxide form) of incorporated modifying metal onto the zeolite catalyst compositions of the present invention.

Generally, the zeolite composites of the present invention can be modified by contacting such composites with solution of compounds of the metals to be incorporated. Such solutions may be formulated from any suitable solvent which is inert with respect to the metal-containing compound and the zeolite composition. Nonlimiting examples of some suitable solvents include water, aromatic and aliphatic hydrocarbons, alcohols, and organic acids (such as acetic acid, formic acid, propionic acid and so forth). Other commonly available solvents such as halogenated hydrocarbons, ketones, ethers, etc., may also be useful to dissolve some metal compounds or complexes. Generally, the most useful solvent will be found to be water. However, the solvent of choice for any particular compound will, of course, be determined by the nature of that compound and for that reason the foregoing list should not be considered exhaustive of all of the suitable possibilities.

The treating compound of the modifying metal may also be used without a solvent, i.e., may be used as a neat liquid. Further, the treating compound may also be utilized in the gaseous phase. As such, it can be used by itself or in admixture with a gaseous diluent, e.g., helium or nitrogen, relatively inert to the treating compound and the zeolite.

Treating compounds are those which contain the elements magnesium, manganese or platinum, the three catalyst modifiers used in the present invention. Representative magnesium-containing compounds include magnesium acetate, magnesium nitrate, magnesium benzoate, magnesium propionate, magnesium 2-ethylhexanoate, magnesium carbonate, magnesium formate, magnesium oxylate, magnesium amide, magnesium bromide, magnesium hydride, magnesium lactate, magnesium laurate, magnesium oleate, magnesium palmitate, magnesium salicylate, magnesium stearate and magnesium sulfide.

Representative manganese-containing compounds include manganese acetate, manganese nitrate, manganese lactate, manganese oxalate, manganese carbonate, manganese citrate, manganese tartarate, manganese bromide, manganese chloride, manganese sulfate, and manganese sulfide.

Representative platinum-containing compounds and complexes include platinum dibromide, platinum carbonyl dichloride, diplatinum dicarbonyl tetrachloride, platinum dichloride, platinum trichloride, platinum hexafluoride, platinum hydroxide, platinum dioxide, platinum pyrophosphate, platinum sulfate, tetraamine platinum chloride and tetraamine platinum salt.

The amount of modifying metal incorporated onto the zeolite composition by reaction with metal-containing compound will depend upon several factors. One of these is the reaction time, i.e., the time that the zeolite composition and the metal-containing source are maintained in contact with each other. With greater reaction times, all other factors being equal, a greater amount of metal is incorporated with the zeolite. Other factors upon which the amount of modifiers incorporated with the zeolite is dependent include reaction temperature, concentration of the treating compound in the reaction mixture, the degree to which the zeolite composition has been dried prior to reaction with the metal-containing compound, the conditions of drying of the zeolite composition after reaction with the treating compound, and the amount and type of binder incorporated with the zeolite composition.

After modifying metal has been incorporated into the zeolite composite to the extent desired, the metal containing composite can be heated subsequent to preparation and prior to use. Such heating can be carried out in the presence of oxygen, for example, in air. Although heating may be carried out at a temperature of about 150° C., higher temperatures, e.g., up to about 500° C., are preferred. Heating is generally carried out for 1–5 hours but may be extended to 24 hours or longer. While heating temperatures above about 500° C. may be employed, they are generally not necessary. After the metal-containing composite is heated in air at elevated temperatures, it is contemplated that the modified metals are actually present at least in part in the zeolite composite in an oxidized state, such as MgO, MnO and combinations of MgO and PtO.

The zeolite composites herein are treated with the foregoing compounds and subsequently heated, under conditions and for a time aufficient to incorporate a minor proportion of the modifying element onto the zeolite composite. Generally, modifying metal oxide is incorporated to the extent of from about 0.5% to 15% by weight of the zeolite composite, preferably from about 1% to 10% by weight of the zeolite, calculated on the basis of the elemental metal. When magnesium oxide is the modifying agent, the composite can advantageously comprise from about 2% to about 8% by weight of magnesium. When manganese oxide is the modifying agent, the zeolite composite can advantageously comprise from about 2% to 8% by weight manganese. When a combination of magnesium oxide and platinum oxide is used as the modifying agent, the zeolite composite can advantageously comprise from about 0.5% to 8% by weight of total magnesium plus platinum.

As noted, the novel metal oxide-modified zeolite catalysts of the present invention are especially useful for the selective conversion of methanol and/or methyl ether to hydrocarbons, particularly light ($C_2$–$C_3$) olefins. Processes of this type are described more fully in U.S. Pat. Nos. 4,079,095 and 4,079,096, the disclosures of which are incorporated herein by reference.

In accordance with the process aspects of the present invention, a chargestock comprising methanol (methyl alcohol), methyl ether, methanol/methyl ether mixtures or mixtures of such organic materials with water can be contacted in the vapor phase with the modified catalyst materials hereinbefore described in a reaction zone and under reaction conditions suitable for effecting conversion of methanol and/or methyl ether to olefins. Such conditions include an operating temperature between about 260° C. (~500° F.) and 540° C. (~1000° F.), preferably 300° C. and 450° C.; a pressure between about 0.1 psi and 300 psi preferably 5 psi and 50 psi; and a weight hourly space velocity (WHSV) of the organic reactants between about 0.1 and 30, preferably 1 and 10. Carrier gases or diluents may be injected into the reaction zone such as, for example, hydrogen, nitrogen, helium, water, carbon monoxide, carbon dioxide, or mixtures of these gases.

When water is employed along with the organic feed, the amount of water fed with the organic charge of methanol and/or methyl ether can be generally at least about 0.25 moles of water per mole of the organic reactants. Preferably, the amount of water added can be greater than about 0.5 moles of water per mole of organic reactants. The amount of water initially added to the organic charge usually will not exceed about 40 moles per mole of said charge.

The methanol and/or methyl ether conversion process described herein may be carried out as a batch-type, semi-continuous or continuous operation utilizing a fixed, fluidized or moving bed catalyst system. A preferred embodiment entails use of a catalyst zone wherein the alcohol or ether charge optionally together with added water is passed concurrently or countercurrently through a fluidized or moving bed of particle-form catalyst. The latter after use may be conducted to a regeneration zone wherein coke is burned from the catalyst in an oxygen-containing atmosphere, e.g., air, at an elevated temperature, after which the regenerated catalyst can be recycled to the conversion zone for further contact with the methanol and/or ether containing feed.

The product stream in the process of the invention contains steam and a hydrocarbon mixture of paraffins and olefins, substantially devoid of aromatics. This mixture is particularly rich in light olefins, i.e., ethylene and propylene. Generally, a major fraction of the total olefins is ethylene plus propylene with the ethylene content of the product exceeding the propylene content. Thus, the predominant hydrocarbon product constitutes valuable petrochemicals. The steam and hydrocarbon products maybe separated from one another by methods well known in the art. In a preferred embodiment of the invention, the unconverted methanol and/or dimethyl ether, as well as at least part of the water in the product, can be recycled to the reaction zone.

The following examples will serve to illustrate the catalysts and processes of this invention without limiting the same.

EXAMPLE I

ZSM-34 is prepared by interacting the following solutions:

A. Caustic Aluminate
 68.89 grams sodium aluminate (20 wt. % Na, 43.1 wt. % $Al_2O_3$, Balance $H_2O$)
 29.28 grams NaOH (77.5 wt. % $Na_2O$)
 26.4 grams KOH 86.4% KOH
 540 grams $H_2O$
B. Silica Solution
 780 grams Colloidal Silica sol (30 Wt. % $SiO_2$)
C. Choline Chloride
 228 grams These are mixed together in a 2 liter autoclave adding solution C to solution A and then adding solution B followed by a 15 minute continuous mixing. The autoclave is then sealed, pressure-tested and then heated to and held at 300° F. for 8 days. The contents are stirred continuously during the 8 day crystallization period.

The autoclave and its contents are cooled to room temperature, and the crystalline product is filtered and washed. On analysis the product is found to contain:
 Na, wt %: 0.68
 K, wt %: 3.59
 $Al_2O_3$ wt %: 13.5
 $SiO_2$, wt % :78.5
 N, wt %: 2.5

The resulting ZSM-34 product has the following molar composition:

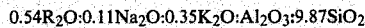

$$0.54R_2O:0.11Na_2O:0.35K_2O:Al_2O_3:9.87SiO_2$$

A sample of the calcined alkali ZSM-34 is further processed by contacting with a 10 wt % $NH_4Cl$ solution for 1 hour at about 185° F. using 10 ml. of solution for each gram of ZSM-34. A total of four contacts are made at these conditions followed by final filtration and water washing essentially free of chloride ion.

The product is dried at 230° F. and calcined for 10 hours at 1000° F. The residual alkali content as Na is 0.035 wt. % while the residual K content is 1.47 wt. %. This product has a surface area of 517 $m^2/g$ and the following sorption capacity:
 Cyclohexane, wt %: 2.6
 n-Hexane, wt %: 10.0
 $H_2O$, wt %: 18.7

EXAMPLE II

ZSM-34 prepared in a manner similar to that of Example I is used to convert methanol to hydrocarbons in known manner. The ZSM-34 used in such conversion had a surface area of 475 $m^2/g$ and the following sorption capacity:
 Cyclohexane, wt %: 4.5
 n-Hexane, wt. %: 9.9
 $H_2O$, wt %: 16.5

In the conversion procedure, two grams of zeolite (no binder) and four grams of quartz chips, both of 14/20 mesh size, were mixed and packed into a quartz microreactor, equipped a with thermocouple. Several cycles were run, and the catalyst was always calcined at 500° C. with air for at least 16 hours before each new cycle. The standard feed contained 37.2% MeOH and 62.8% $H_2O$ (by weight). The methanol/water mixture was fed to the reactor maintained at 370° C. and 1 atmosphere using a weight hourly space velocity (WHSV) of 4.1. The total reactor effluent is analyzed, on line, by a "n-octane on Poracil" column. Methanol conversion is calculated based on hydrocarbon formation only. Selectivities (wt %) to hydrocarbon product are calculated on "coke free" basis.

The lifetimes for converting 50% of the methanol for each cycle and the corresponding selectivities to $C_2H_4$, $C_3H_6$ and $C_4H_8$ are summarized in Table I.

TABLE I

Catalyst Lifetimes and Selectivities to $C_2H_4$, $C_3H_6$ and $C_4H_8$ by HZSM-34 at 50% MeOH Conversion

| Cycle # | 1 | 2 | 3 | 4 |
|---|---|---|---|---|
| Lifetime for 50% MeOH Conversion, (hours) | 2.6 | 2.0 | 1.7 | 1.4 |
| Selectivities (wt %) at 50% MeOH Conversion | | | | |
| $C_2H_4$ | 61 | 56 | 58 | 55 |
| $C_3H_6$ | 25 | 26 | 29 | 28 |
| $C_4H_8$ | 4 | 7 | 7 | 7 |
| Total $C_2= - C_4=$ | 90 | 89 | 94 | 90 |

The Table I data demonstrate that HZSM-34 provides relatively high selectivity to light olefins for conversion of a methanol/water feed to hydrocarbons. Such data also indicate that catalyst lifetime or methanol conversion over HZSM-34 is relatively short.

EXAMPLE III

HZSM-34 is modified by incorporating magnesium oxide onto the zeolite in the following manner. Two grams of the 14/20 mesh HZSM-34 as prepared in Example I were soaked overnight in an aqueous solution containing 5 grams $Mg(OAc)_2.4H_2O$ and 10 grams distilled water at room temperature. The catalyst pellets were then filtered, dried in air and further dried in an oven at 100° C. for 2 hours. The final MgZSM-34, after calcination at 500° C. in air for 16 hours, weighs 2.2 g. Catalyst treated in this manner contains about 4.0% by weight magnesium present at least in part in the form of magnesium oxide.

EXAMPLE IV

The magnesium oxide modified ZSM-34 prepared as described in Example III is used to promote conversion of methanol to hydrocarbons in the same general manner as described in Example II. The methanol/water mixture was fed to the reactor at 400° C./1 atmosphere using a WHSV of 2.1. Five cycles were run. The lifetimes for converting 50% of the methanol for each cycle and the corresponding selectivities to $C_2H_4$, $C_3H_6$ and $C_4H_8$ are summarized in Table II.

TABLE II

Catalyst Lifetimes and Selectivities to $C_2H_4$, $C_3H_6$ and $C_4H_8$ by MgZSM-34 at 50% MeOH Conversion

| Cycle # | 1 | 2 | 3 | 4 | 5 |
|---|---|---|---|---|---|
| Lifetime for 50% MeOH Conversion, (hours) | 8.8 | 8.2 | 7.2 | 7.8 | 9.8 |
| Selectivities (wt %) at 50% MeOH Conversion | | | | | |
| $C_2H_4$ | 63 | 60 | 62 | 63 | 64 |
| $C_3H_6$ | 25 | 26 | 26 | 24 | 21 |
| $C_4H_8$ | 4 | 3 | 4 | 4 | 4 |

TABLE II-continued

Catalyst Lifetimes and Selectivities to $C_2H_4$, $C_3H_6$
and $C_4H_8$ by MgZSM-34 at 50% MeOH Conversion

| Total $C_2=-C_4=$ | 94 | 89 | 92 | 91 | 89 |
|---|---|---|---|---|---|

The Table II data in comparison with that of Table I indicate that magnesium modified HZSM-34 improved the catalyst lifetime to 7.2–9.8 hours. The selectivities to $C_2H_4$ and total light olefins were not changed by such catalyst modification.

EXAMPLE V

HSZM-34 was modified by incorporating manganese oxide onto the zeolite in a manner similar to that described in Example II for the preparation of MgZSM-34. In such a procedure $Mn(OAc)_2.4H_2O$ was used in place of the $Mg(OAc)_2.4H_2O$ employed in preparation of MgZSM-34. The resulting manganese treated zeolite contained at least about 2% by weight manganese present at least in part in the form of manganese oxide.

EXAMPLE VI

The manganese oxide modified ZSM-34 prepared as described in Example V was used to promote conversion of methanol to hydrocarbons in the same general manner as described in Example II. In such a reaction, the methanol/water mixture was fed to the reactor at 390° C. and 1 atmosphere using a WHSV of 2.1. One cycle was run for which the catalyst lifetime for 50% methanol conversion is 9 hours, and the selectivities to $C_2H_4$, $C_3H_6$ and $C_4H_8$ at 50% methanol conversion was 56%, 30% and 3%, respectively.

EXAMPLE VII

HSZM-34 is modified by incorporating both magnesium oxide and platinum oxide onto the zeolite in the following manner. Two grams HZSM-34 of 14/20 mesh prepared in the same general manner as in Example I are gently refluxed in 10 cc aqueous solution containing 0.006 g $Pt(NH_3)_4Cl_2$ for 8 hours. The dried zeolite is then soaked in dilute aqueous $Mg(OAc)_2$ (10%) solution for 16 hours at room temperature. The zeolite is filtered, dried and calcined in air at 500° C. Zeolite catalyst prepared in this manner contains at least about 0.25% by weight magnesium at least in part as magnesium oxide and about 0.25% by weight platinum at least in part as platinum oxide.

EXAMPLE VIII

The magnesium oxide/platinum oxide modified ZSM-34 prepared as described in Example VII is used to promote conversion of methanol to hydrocarbons in the same general manner as described in Example II. In such a reaction the methanol/water mixture is fed to the reactor at 370° C./1 atmosphere using a WHSV of 2.1. Hydrogen is cofed to the reactor at a WHSV for $H_2$ of 0.02. One cycle is run for which the catalyst lifetime for 50% methanol conversion is 7.5 hours, and the selectivities to $C_2H_4$, $C_3H_6$ and $C_4H_8$ are 59%, 27% and 5%, respectively.

Examples VI and VIII show that modification of HZSM-34 with manganese oxide or a combination of magnesium oxide and platinum oxide can improve the catalyst lifetime and maintain the high selectivity to $C_2H_4$ and total light olefin formation for methanol conversion.

EXAMPLE IX

A synthetic offretite is prepared by interacting the following solutions:

| Silicate solution: | Q-Brand | 960 g |
|---|---|---|
| | KOH (88%) | 119.5 g |
| | $H_2O$ | 1050 g |
| Alum Solution: | $Al_2(SO_4)_3$ $XH_2O$ | 100.5 g |
| | KCl | 107 g |
| | $H_2O$ | 550 g |
| Tetramethylammonium chloride (50%) | | 128.6 g |

The above silicate and alum solutions are mixed in a Waring blender for 10 minutes. The resultant gel is aged at ambient temperatures for four hours, then is transferred to a 1 gallon autoclave. TMA Cl is added to the gel. The mixture is crystallized at 210° F. with stirring for about 65 hours. The product mixture is filtered, washed and dried. The product is TMA offretite, as shown by x-ray diffraction pattern. The crystal size of the product is 0.040–0.2 micron.

The dried zeolite is precalcined at 1000° F. in flowing $N_2$ for 3 hours, followed by $NH_4NO_3$ exchange to reduce NA content in zeolite. The sample is sized into 14/20 mesh and air calcined at 1000° F. for 3 hours. The final product is analyzed and found to contain 0.02% weight Na and 2.4% weight K.

Two grams of the synthetic offretite so synthesized is then soaked in an aqueous solution containing 5 grams of $Mg(OAc)_2.4H_2O$ and 10 grams of distilled water at room temperature overnight. The catalyst pellets are then filtered, dried in air and further dried in an oven at 100° C. for 2 hours. The final Mg offretite after calcination in air at 500° C. for 16 hours, contains at least about 20% by weight of magnesium present at least in part in the form of magnesium oxide. Such a modified offretite zeolite is an effective catalyst for the selective conversion of methanol or methyl ether to light olefins with improved catalyst lifetime in comparison to similar offretite material containing no magnesium oxide.

EXAMPLE X

Synthetic erionite is prepared by interacting the following solutions:

A.

Sodium Aluminate Solution
98.2 g $NaAlO_2$ (41.8 wt % $Al_2O_3$, 33.1 wt % $Na_2O$)
1680 ml $H_2O$
208 g NaOH 97 wt %
42.4 g KOH 85.5 wt %

B.

Colloidal Silica
234 g Colloidal Silica (30 wt % $SiO_2$)

C. Benzyltrimethyl Ammonium Chloride 142 g 60 wt % solution

These are mixed together adding C to A and then adding B. After mixing for 15 minutes the slurry is transferred to two polypropylene jars and reacted in a 212° F. bath for 68 days.

The adsorption capacity of a sample and the resulting crystalline synthetic erionite after calcination for 10 hours at 1000° F. is:

Cyclohexane, wt %: 1.0
n-Hexane, wt %: 8.4
$H_2O$: 16.6

$m^2/g$ is 447

The synthetic erionite as prepared above is calcined for 10 hours at 1000° F. and then contacted 4 times with 113 ml of 0.5N $NH_4Cl$ solution at 190°–195° F. The exchanged zeolite is water washed essentially free of chloride ion, dried at 230° F., pelleted and sized 14–25 mesh and then calcined for 10 hours at 1000° F. The residual sodium content is 0.18 weight percent.

The synthetic erionite as prepared above is further modified to incorporate magnesium oxide onto the zeolite. Two grams of the synthetic erionite pellets are soaked in an aqueous solution containing 5 grams $Mg(OAc).4H_2O$ and 10 grams distilled water at room temperature overnight. The catalyst pellets are then filtered, dried in air and further dried in an oven at 100° C. for 2 hours. The final Mg-erionite, after calcination at 500° C. in air for 16 hours, contains at least about 2% by weight magnesium present at least in part as magnesium oxide. Such a modified erionite zeolite is an effective catalyst for the selective conversion of methanol or methyl ether to light olefins with improved catalyst lifetime in comparison to similar erionite material containing no magnesium oxide.

EXAMPLE XI

Zeolite T is prepared in accordance with Example 1 of U.S. Pat. No. 2,950,952. The sorption capacity of a sample of the resulting Zeolite T calcined at 1000° F. is as follows:

Cyclohexane, wt %: 0.9
n-Hexane, wt %: 2.0
$H_2O$, wt %: 12.6

The above alkali zeolite is subsequently processed by calcining in air for 10 hours at 1000° F. then exchanged for 2–4 hours by contacts with 5M $NH_4Cl$ at 180° F. using 6 ml of solution per gram of zeolite. This treatment is followed by water washing essentially free of Cl ion, drying and recalcining for 10 hours at 1000° F. The base exchange step is repeated again to reduce the residual alkali to low level. The water washed exchanged zeolite is air dried at 230° F., pelleted and sized 14–25 mesh and recalcined for 10 hours at 1000° F.

An analysis of the final zeolite shows the following compositions:

Na, wt %: 0.075
K, wt %: 1.65
$Al_2O_3$, wt %: 18.7
$SiO_2$, wt %: 78.8
Molar Ratio $SiO_2/Al_2O_3$ 7.2

The sorption capacity is as follows:

Cyclohexane, wt %: 0.6
n-Hexane, wt %: 5.7
$H_2O$, wt %: 13.1
Surface area is 199 $m^2/g$ Zeolite T as prepared above is modified to incorporate magnesium oxide onto the zeolite. Two grams of the Zeolite T pellets are soaked in an aqueous solution containing 5 g of $Mg(OAc)_2.4H_2O$ in 10 g of distilled water or 16 hours at room temperature. The zeolite is filtered, dried and calcined in air at 500° C. Zeolite catalyst prepared in this manner contains at least about 2% by weight magnesium as magnesium oxide. Such a modified Zeolite T zeolite is an effective catalyst for the selective conversion of methanol or methyl ether to light olefins with improved catalyst lifetime in comparison to similar Zeolite T material containing no modifying oxide.

What is claimed is:

1. A catalytic process for converting with enhanced catalyst lifetime a feedstock comprising methanol, methyl ether or mixture thereof to a hydrocarbon product rich in ethylene and propylene, which process comprises contacting said feedstock under conversion conditions including a temperature between about 260° C. and 540° C., a pressure between about 0.1 psi and 300 psi and a weight hourly space velocity of the organic reactants of between about 0.1 and 30, with a catalyst comprising a ZSM-34 crystalline aluminosilicate zeolite material, said catalyst further having incorporated thereon a catalyst lifetime enhancing amount of a catalyst modifier selected from magnesium oxide, manganese oxide and combinations of magnesium oxide and platinum oxide, wherein said catalyst modifier is incorporated onto said catalyst by the steps of:

(i) contacting the catalyst with a solution of the metal or metals to be incorporated thereon, whereby at least a portion of said metal or metals is adsorbed or impregnated onto said catalyst, said adsorbed or impregnated metal or metals not being incorporated onto the catalyst by an ion exchange mechanism; and (ii) heating said catalyst of step (i) in the presence of oxygen to convert said adsorbed or impregnated metal or metals to an oxide or oxides thereof.

2. A process according to claim 1 wherein said catalyst modifier is magnesium oxide and is present in an amount sufficient to provide from about 1% to 10% by weight magnesium on said catalyst.

3. A process according to claim 1 wherein said catalyst modifier is manganese oxide and is present in an amount sufficient to provide from about 1% to 10% by weight of manganese of said catalyst.

4. A process according to claim 1 wherein said catalyst modifier is a combination of magnesium oxide and platinum oxide present in an amount sufficient to provide from about 0.5% to 8% by weight total magnesium plus platinum on said catalyst.

5. A process according to claim 1 wherein said conversion conditions include a temperature from about 300° C. to 450° C., a pressure of from about 5 psi to 50 psi and a weight hourly space velocity of from about 1 to 10.

6. A process according to claim 5 wherein said feedstock also comprises water present in an amount of at least about 0.25 mole of water per mole of organic reactants.

7. A process according to claim 1 wherein said zeolite is combined with a binder therefor.

* * * * *